(12) United States Patent
Pearlman

(10) Patent No.: US 6,362,334 B1
(45) Date of Patent: Mar. 26, 2002

(54) PHTHALAMIDE COMPOUNDS

(75) Inventor: Bruce Allen Pearlman, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/546,357

(22) Filed: Apr. 10, 2000

Related U.S. Application Data

(62) Division of application No. 09/170,776, filed on Oct. 13, 1998, now Pat. No. 6,107,519.
(60) Provisional application No. 60/064,738, filed on Nov. 7, 1997.

(51) Int. Cl.$^7$ ...................... C07D 403/12; C07D 413/12
(52) U.S. Cl. ........................................ 544/144; 544/373
(58) Field of Search ................................. 544/144, 373

(56) References Cited

U.S. PATENT DOCUMENTS

| | | |
|---|---|---|
| 3,654,298 A | 4/1972 | Douzon et al. |
| 4,150,029 A | 4/1979 | Dostert et al. |
| 4,250,318 A | 2/1981 | Dostert et al. |
| 4,340,606 A | 7/1982 | Fugitt et al. |
| 4,402,981 A | 9/1983 | Liepmann et al. |
| 4,461,773 A | 7/1984 | Gregory |
| 4,476,136 A | 10/1984 | Dostert et al. |
| 4,948,801 A | 8/1990 | Carlson et al. |
| 5,164,510 A | 11/1992 | Brickner |
| 5,182,403 A | 1/1993 | Brickner |
| 5,225,565 A | 7/1993 | Brickner |
| 5,231,188 A | 7/1993 | Brickner |
| 5,244,901 A | 9/1993 | Pascal et al. |
| 5,247,090 A | 9/1993 | Brickner |
| 5,332,754 A | 7/1994 | Nakai et al. |
| 5,547,950 A | 8/1996 | Hutchinson et al. |
| 5,565,571 A | 10/1996 | Barbachyn et al. |
| 5,663,173 A | 9/1997 | Jegham et al. |
| 5,688,792 A | 11/1997 | Barbachyn et al. |

OTHER PUBLICATIONS

Patent Abstract of Japan vol. 5(4) [C–038]–Jan. 13, 1981—JP 55 133357 A.

Barbachyn, M.R. et al., "Identification of a Novel Oxazolidinone (U–100480) with Potent Antimycobacterial Activity," J. Med. Chem 39:680–685 (1996).

Brickner, S.J., et al. "Synthesis and Antibacterial Activity of U–100592 and U–100766, Two Oxazolidinone Antibacterial Agents for the Potential Treatment of Multidrug–Resistant Gram–Positive Bacterial Infections," J. Med. Chem. 39:673–679 (196).

Gregory, W.A., et al., "Antibacterials. Synthesis and Structure–Activity Studies of 3–Aryl–2–oxooxazolidines. 2. The "A" Group," J. Med. Chem. 33–2569–2578 (1990).

Schaus, S.E. and E.N. Jacobsen, "Dynamic Kinetic Resolution of Epichlorohydrin via Enantioselective Catalytic Ring Opening with TMSN, Practical Synthesis of Aryl Oxazolidinone Antibacterial Agents," Tetrahedron Letters 37(44):7937–7940 (1996).

Wang, C–LJ et al., "Chiral Synthesis of DUP 721, A New Antibacterial Agent," Tetrahedron 45(5):1323–1326 (1989).

Barbachyn, M.R., et al., "Synthesis and Structure–Activity Relationships of New Tropone–Substituted Oxazolidinone Antibacterial Agents," Abstract of Papers (F206), 35$^{th}$ Interscience Conference on Antimicrobial Agents and Chemotherapy, San Francisco, CA, September 1995; American Society for Microbiology: Washington, DC, 1995.

Hutchinson, D.K. et al., "Piperazinyl Oxazolidinones: Structure Activity Relationships of a New Class of Oxazolidinone Antibacterial Agents," Abstract of Papers (F207), 35$^{th}$ Interscience Conference on Antimicrobial Agents and Chemotherapy, San Francisco, CA, September 1995; American Society for Microbiology: Washington, DC, 1995.

Brickner, S.J. et al., Synthesis of U–100592 and U–100766, Two New Oxazolidinone Antibacterial Agents in Clinical Trials for Treatment of Multiply Resistant Gram Positive Infections, Abstract of Papers (F208), 35$^{th}$ Interscience Conference on Antimicrobial Agents and Chemotherapy, San Francisco, CA, September 1995; American Society for Microbiology: Washington, DC, 1995.

Barbachyn, M.R. et al., Identification of New Oxazolidinone Antibacterial Agents with Potent In Vitro Antimycobacterial Activity, Abstract of Papers (F227), 35$^{th}$ Interscience Conference on Antimicrobial Agents and Chemotherapy, San Francisco, CA, September 1995; American Society for Microbiology: Washington, DC, 1995.

Gregory, W.A., et al., "Antibacterials. Synthesis and Structure–Activity Studies of 3–Aryl–2–oxooxazolidines. 1. The "B"Group," J. Med. Chem. 32:1673–1681 (1989).

Primary Examiner—Robert W. Ramsuer
(74) Attorney, Agent, or Firm—Bruce Stein; John H. Engelmann

(57) ABSTRACT

The present invention includes a number of novel intermediates such as the (S)-secondary alcohol of formula (VIIIA)

$$X_2-CH_2-C^*H(OH)-CH_2-NH-CO-R_N \quad (VIIIA)$$

and processes for production of pharmacologically useful oxazolidinones.

3 Claims, No Drawings

PHTHALAMIDE COMPOUNDS

CROSS-REFERENCE TO RELATED APPLICATIONS

The present Application is a divisional of U.S. patent application Ser. No. 09/170,776, filed Oct. 13, 1998, now U.S. Pat. No. 6,107,519 which claims the benefit of U.S. provisional application Ser. No. 60/064,738 filed Nov. 7, 1997.

BACKGROUND OF THE INVENTION

1. Field of the Invention

The present invention is a process to prepare pharmacologically active oxazolidinones and various intermediates used in the process.

2. Description of Related Art

Various 5-acetamidomethyloxazolidinones are well known to those skilled in the art as pharmacologically useful antibactericals. Various methods are well known to those skilled in the art for preparing these useful therapeutic agents.

U.S. Pat. Nos. 5,164,510, 5,182,403 and 5,225,565 disclose 5'-indolinyloxazolidinones, 3-(5'-indazolyl) oxazolidinones, 3-(fused-ring substituted) phenyloxazolidinones respectively useful as antibacterial agents.

U.S. Pat. Nos. 5,231,188 and 5,247,090 disclose various tricyclic [6.5.5] and [6.6.5]-fused ring oxazolidinones useful as antibacterial agents.

International Publication WO93/09103 discloses mono- and di-halo phenyl oxazolidinone anti-bacterials which are useful as pharmaceutical agents for their anti-bacterial action.

Prior art processes to make oxazolidinones involve condensation of an aromatic carbamate with a non-nitrogen caontaining three-carbon reagent to give an intermediate oxazolidinone with a hydroxymethyl substituent at the 5-position. The hydroxyl must then be replaced by an acetamido group to give the pharmacologically active 5-acetamidomethyloxazolidinones. Many variants of this essentially two-step process have been developed.

U.S. Pat. Nos. 4,150,029, 4,250,318, 4,476,136, 4,340,606 and 4,461,773 disclose the synthesis of 5-hydroxymethyloxazolidinones from amines (R—NHX$_1$, where X$_1$ is —H or p-toluenesulfonyl) and R,S-glycidol (C$^\#$H$_2$—O—C$^\#$H—CH$_2$—OH where the carbon atoms marked $^\#$ are bonded together, cyclized to form an epoxide). The mixture of enantiomers produced by this process (represented by the formula R—NH—CH$_2$—CHOH—CH$_2$—OH) are separated by fractional crystallization of the mandelic acid salts. The enantiomerically pure R-diol is then converted into the corresponding 5R-hydroxymethyl substituted oxazolidinones by condensation with diethylcarbonate in the presence of sodium methoxide. These 5R-hydroxymethyl substituted oxazolidinones must be aminated in a subsequent step.

J. Med. Chem., 32, 1673 (1989), Tetrahedron 45, 1323 (1989) and U.S. Pat. No. 4,948,801 disclose a method of producing oxazolidinones which comprises reacting an isocyanate (R—N═C═O) with (R)-glycidyl butyrate in the presence of a catalytic amount of lithium bromide-tributylphosphine oxide complex to produce the corresponding 5R-butyryloxymethyl substituted oxazolidinone. The process is performed at 135–145°. The butyrate ester is then hydrolyzed in a subsequent step to give the corresponding 5R-hydroxymethyl substituted oxazolidinone. The 5R-hydroxymethyl substituted oxazolidinone must then be aminated in a subsequent step.

Abstracts of Papers, 206th National Meeting of the American Chemical Society, Chicago, Ill., August, 1993; American Chemical Society: Washington, D.C., 1993; ORGN 089; J. Med. Chem. 39, 673 (1996); J. Med. Chem. 39, 680 (1996); International Publications WO93/09103, WO93/09103, WO95/07271 and WO93/23384; PCT applications PCT/US95/12751 and PCT/US95/10992; Abstracts of Papers, 35th Interscience Conference on Antimicrobial Agents and Chemotherapy, San Francisco, Calif., September, 1995; American Society for Microbiology: Washington, D.C., 1995; Abstract No. F208; Abstracts of Papers, 35th Interscience Conference on Antimicrobial Agents and Chemotherapy, San Francisco, Calif., September, 1995; American Society For Microbiology: Washington, D.C., 1995; Abstract No. F207; Abstracts of Papers, 35th Interscience Conference on Antimicrobial Agents and Chemotherapy, San Francisco, Calif., September, 1995; American Society for Microbiology: Washington, D.C., 1995; Abstract No. F206; Abstracts of Papers, 35th Interscience Conference on Antimicrobial Agents and Chemotherapy, San Francisco, Calif., September, 1995; American Society for Microbiology: Washington, D.C., 1995; Abstract No. F227; disclose the reaction of a carbamate with n-butyllithium, lithium diisopropylamide or lithium hexamethyldisilazide at −78° to −40° followed by glycidyl butyrate at −78° followed by warming to 20–25° to produce 5R-hydroxymethyl substituted oxazolidinones where the ester is cleaved during the reaction. The 5R-hydroxymethyl substituted oxazolidinones must then be aminated in a subsequent step.

International Publication WO95/07271 discloses the ammonolysis of 5R-methylsulfonyloxymethyl substituted oxazolidinones.

U.S. Pat. No. 4,476,136 discloses a method of transforming 5-hydroxymethyl substituted oxazolidinones to the corresponding 5(S)-aminomethyl substituted oxazolidinones (VII) that involves treatment with methane sulfonyl chloride followed by potassium phthalimide followed by hydrazine.

J. Med. Chem., 32, 1673 (1989) and Tetrahedron 45, 1323 (1989) disclose a method for transforming 5-hydroxymethylsubstituted oxazolidinones into the corresponding 5S-acetamidomethyl substituted oxazolidinones that involves treatment with methanesulfonyl chloride or tosyl chloride, followed by sodium azide, followed by trimethylphosphite or platinum dioxide/hydrogen, followed by acetic anhydride or acetyl chloride to give the desired 5(S)-acetamidomethyl substituted oxazolidinone.

U.S. Pat. No. 5,837,870 discloses a process to prepare 5(S)-hydroxymethyl substituted oxazolidinone intermediates which are useful in the preparation of the pharmacologically active 5(S)-acetamidomethyloxazolidinoes. It further discloses a process to convert the 5-hydroxymethyl substituted oxazolidinone intermediates into 5-aminomethyl substituted oxazolidinone intermediates which can be acylated to produce the pharmacologically active 5(S)-acetamidomethyl substituted oxazolidinones.

J. Med. Chem., 33, 2569 (1990) discloses the condensation of an isocyanate with racemic glycidyl azide to produce a racemic 5-azidomethyl-substituted oxazolidinone. Two subsequent steps are required to convert the racemic azidomethyl-substituted oxazolidinone into racemic 5-acetamidomethyl-substituted oxazolidinone, which has antibiotic activity. The present invention converts isocyanates into the (S)-enantiomer of acetamidomethyl-substituted oxazolidinones which have greater antibiotic activity than the racemates, in one step.

U.S. Pat. No. 5,332,754 discloses (col. 2, lines 14–34) that racemic oxazolidinone-$CH_2$—NH—Ac can be synthesized in one step by condensation of a carbamate with racemic glycidyl acetamide "in the presence of a base" such as an amine, "alkali metal hydroxide, an alkali metal alkoxide, and the like", and that "it is preferred to carry out the reaction under heating . . . preferably at a temperature between 90° C. and 110° C." (col. 4, lines 44–56). Evidence indicates that under these conditions rearrangement to an undesired product occurs. The patent provides no yields or description of this process in the Examples. Indeed, the EXAMPLEs disclose not a one-step process but multi-step routes that are known to those skilled in the art involving mesylation of a 5-hydroxymethyl substituted oxazolidinone followed by azide displacement, hydrogenation and acetylation of the amine. In particular, see EXAMPLEs 59–63. The present invention differs in that the contacting between the carbamate (IX) and the epoxide (VIIIB) is performed under conditions that competing rearrangement to the undesired side products is largely suppressed.

*Tetrahedron Letters*, 37, 7937–40 (1996) discloses a sequence for synthesis of S-glycidylacetamide ($R^2$=—NHAc) and a process for condensation of a carbamate with 1.1 equivalents of n-butyl lithium (THF, −78°) followed by 2 equivalents of S-glycidylacetamide to give the corresponding 5S-acetamidomethyl-substituted oxazolidinone. The present invention differs in that the contacting between the carbamate (IX) and S-glydidylacetamide is performed in the presence of lithium alkoxide bases or the carbamate (IX) is contacted with the S-chlorohydrin acetamide (VIIIA) or S-chloroacetate acetamide (VIIIC) or an isocyanate (XIV) is contacted with the S-chlorohydrin acetamide (VIIIA).

U.S. Pat. No. 3,654,298 discloses the synthesis of 5-alkoxymethyl-3-aryl-substituted oxazolidinones by sodium ethoxide induced cyclization of chlorocarbamates. The present invention differs in that the substituent at the 5-position is acylamino.

SUMMARY OF THE INVENTION

Disclosed is an (S)-secondary alcohol of formula (VIIIA), an (S)-epoxide of formula (VIIIB), an (S)-ester of formula (VIIIC), an (S)-protected alcohol of the formula (IVA), an (S)-phthalimide alcohol of formula (IVC), and (S)-phthalimide epoxide of formula (IVD), an (S)-imine of glydidylamine of formula (IVB), an (S)-intermediate of formula (XV) and an (S)-oxazolidinone phthalamide intermediate of formula (XVI).

Also disclosed is a process for the preparation of a (S)-3-carbon amino alcohol of the formula (V) which comprises (1) contacting a non-nitrogen adduct of formula (I) with aqueous ammonia (II) in the presence of an (S)-protected-epoxide of formula (III) and (2) contacting the reaction mixture of step (1) with acid.

Further disclosed is a process for the preparation of an (S)-3-carbon amino alcohol of the formula (V) which comprises (1) contacting a phthalimide of formula (VI) with an (S)-protected-epoxide of formula (III) in the presence of potassium phthalamide in DMF or DMAC to give an (S)-phthalimide alcohol of formula (IVC) and (2) contacting the product of step (1) with aqueous acid.

Additionally disclosed is a process for the preparation of a secondary alcohol of the formula (VIIIA) which comprises (1) contacting an (S)-3-carbon amino alcohol of the formula (V) with an acylating agent and a tri(alkyl)amine.

Disclosed is a process for the production of an (S)—oxazolidinone—$CH_2$—NH—CO—$R_N$ of formula (X) which comprises (1) contacting a carbamate of formula (IX) with an oxygenated amino reagent selected from the group consisting of an (S)-secondary alcohol of the formula (VIIIA), an (S)-epoxide of the formula (VIIIB) or an (S)-ester of the formula (VIIIC) in the presence of a lithium cation and a base whose conjugate acid has a $pK_a$ of greater than about 8.

Also disclosed is a process for the production of an (S)—oxazolidinone—$CH_2$—NH—CO—$R_N$ of formula (X) which comprises (1) contacting a carbamate of formula (IX) with a phthalimide alcohol of the formula (IVC) or a phthalimide epoxide of the formula (IVD), in the presence of a lithium cation and a base whose conjugate acid has a $pK_a$ of greater than about 8, (2) contacting the product of step (1) with aqueous acid, (3) contacting the reaction mixture of step (2) with an acid anhydride of the formula O(CO—$R_N$)$_2$ or an acid halide of the formula $R_N$—CO—$X_4$ and a tri(alkyl)amine where alkyl is $C_1$–$C_5$.

Further disclosed is a process for the production of an (S)—$R_{oxa}$—RING—$CH_2$—NH—CO—$R_N$ of the formula (X) which comprises (1) contacting a carbamate of the formula (IX) with a compound selected from the group consisting of a (S)-protected alcohol of the formula (IVA) or a (S)-3-carbon protected epoxide of the formula (IVB) in the presence of a lithium cation and a base whose conjugate acid has a $pK_a$ of greater than about 8 to produce a (S)-protected oxazolidinone of the formula (XII), (2) contacting the reaction mixture of step (1) with aqueous acid to produce an (S)-oxazolidinone free amine of the formula (XIII) and (3) contacting the product of step (2) with an acylating agent selected from the group consisting of an acid anhydride of the formula O(CO—$R_N$)$_2$ or an acid halide of the formula $R_N$—CO—$X_4$ and where $R_N$ is as defined above and a tri(alkyl)amine where alkyl is $C_1$–$C_5$ where $R_{oxa}$ is as defined above.

Additionally disclosed is a process for the production of an (S)—$R_{oxa}$—RING—$CH_2$—NH—CO—$R_N$ of the formula (X) which comprises (1) contacting a carbamate of the formula (IX) in the presence of a lithium cation and a base whose conjugate acid has a $pK_a$ of greater than about 8 to produce an (S)-oxazolidinone free amine of the formula (XIII), and (2) acylating the (S)-oxazolidinone free amine (XIII) with an acylating agent selected from the group consisting of an acid anhydride of the formula O(CO—$R_N$)$_2$ or an acid halide of the formula $R_N$—CO—$X_4$ and a tri(alkyl)amine where alkyl is $C_1$–$C_5$.

DETAILED DESCRIPTION OF THE INVENTION

The present invention includes both novel intermediates and processes useful in the production of commercially valuable oxazolidinone antibiotics (X. One of the novel processes is set forth in CHART D and is the reaction of a carbamate (IX) with either a (S)-secondary alcohol (VIIIA) or (S)-epoxide (VIIIB) or (S)-ester (VIIIC) to produce the corresponding pharmacologically active (S)—oxazolidinone—$CH_2$—CO—$R_1$ (X). A second process to produce the pharmacologically active (S)—oxazolidinone—$CH_2$—CO—$R_1$ (X) is set forth in CHART H and involves reaction of an isocynate (XIV) with a (S)-secondary alcohol (VIIIA) to give the (S)-intermediate (XV) which is then readily transformed to the corresponding pharmacologically active (S)—oxazolidinone—$CH_2$—CO—$R_1$ (X).

The three carbon nitrogen containing fragments (S)-secondary alcohol (VIIIA), (S)-epoxide (VIIIB) and (S)- ester (VIIIC) can be produced in two differet ways. This fragment produces the two adjacent carbon atoms of the oxazolidinone ring, the methylene carbon atom attached thereto as well as the nitrogen containing fragments (S)-secondary alcohol (VIIIA), (S)-epoxide (VIIIB) and (S)-ester (VIIIC) are produced according to the processes of CHART C.

CHART A discloses a process to prepare the (S)-3-carbon amino alcohol (V) from the (S)-$X_2$-epoxide (III) using a non-nitrogen containing adduct (I) and ammonia (II) as the source of nitrogen. In the (S)-$X_2$-epoxide (III), and other compounds of this invention # indicates that the atoms marked with a (#) are bonded to each other resulting in the formation of a ring (epoxide). For the (S)-$X_2$-epoxides (III) it is preferred that $X_2$ be —Cl. The (S)-$X_2$-epoxides (III) are either known to those skilled in the art or can readily be prepared from compounds known to those skilled in the art by methods known to those skilled in the art. For the non-nitrogen containing adduct (I) it is preferred that $X_0$ is —ϕ; it is more preferred that $X_0$ is -ϕ. The reaction of the non-nitrogen adduct (I), ammonia (II) and the (S)-$X_2$-epoxide (III) is performed as set forth in EXAMPLEs 1 and 14. It should be noted that if one starts with enantiomerically pure (S)-$X_2$-epoxide (III) that one then obtains enantiomerically pure (S)-protected alcohol (IVA). The absolute configuration of the carbon atom in the pharmacologically useful (S)—oxazolidinone—$CH_2$—CO—$R_1$ (X) product is "S" and therefore it is preferable to begin with enantiomerically pure (S)-$X_2$-epoxide (III) and obtain enantiomerically pure (S)-protected alcohol (IVA), see CHART A. In the CHARTS and CLAIMS the suprascripted "*" as –C*(a)(b)– denotes the asymetric carbon atom has the appropriate enantiomeric configuration (S)- such that when this carbon atom becomes part of the (S)—oxazolidinone—$CH_2$—CO—$R_1$ (X), it is the correct enantiomer. If one begins any of the chemical sequences of the processes of the present invention with an optically impure (racemic) form rather than an enantiomerically pure form, it is apparent to one skilled in the art that the products obtained will be the corresponding optically impure (racemic) forms.

The (S)-protected alcohol (IVA) is then contacted with an acid to form the corresponding (S)-3-carbon amino alcohol (V). Neither the nature, strength nor amount of the acid is critical. It is preferred that the acid have a $pK_a$ less than 4. It is immaterial whether the acid is organic or inorganic. The (S)-3-carbon amino alcohol becomes the cation and the nonproton portion of the acid is the anion. For example if the mixture is acified with sulfuric acid the (S)-3-carbon amino alcohol (V) is obtained as the sulfate salt. The nature of the anion is not important.

CHART B discloses a way to prepare the desired (S)-3-carbon amino alcohol (V) from the same (S)-$X_2$-epoxide (III) but using a nitrogen containing adduct (VI). In this situation, no ammonia (II) is needed. In the final step of the process, where the product of step one is contacted with aqueous acid, it is preferred that the acid be hydrochloric, hydrobromic, hydroiodic, sulfuric or p-toluenesulfonic acid.

CHART C discloses the process to convert the (S)-3-carbon amino alcohol (V) to the corresponding (S)-secondary alcohol (VIIIA), (S)-epoxide (VIIIB) or (S)-ester (VIIIC) and the conversion of the (S)-secondary alcohol (VIIIA) to the corresponding (S)-epoxide (VIIIB) and (S)-ester (VIIIC) respectively. To convert the (S)-3-carbon amino alcohol (V) to the corresponding (S)-secondary alcohol (VIIIA) the 3-carbon amino alcohol (5) is reacted with an appropriate acylating reagent such as an acyl halide or acyl anhydride under acylation reaction conditions well known to those skilled in the art, see EXAMPLE 2. It is preferred that the acylating reagent be selected from the group consisting of an acid anhydride of the formula $O(CO-R_N)_2$ where $R_N$ is $C_1-C_5$ alkyl or an acid halide of the formula $R_N$—CO—$X_4$ where $X_4$ is —Cl or —Br and a tri(alkyl)amine where alkyl is $C_1-C_5$. It is more preferred that $R_N$ is $C_1$ alkyl and $X_4$ is —Cl. It is more preferred that the acylating reagent be the acyl anhydride and it is preferred that the acyl anhydride be acetic anhydride.

Alternatively, the (S)-epoxide (VIIIB) can be obtained by reaction of the (S)-ester (VIIIC) with bases such as sodium methoxide or potassium carbonate/methanol. Also the (S)-3-carbon amino alcohol (V) can be transformed to the corresponding (S)-ester (VIIIC) by reaction with acetic anhydride in pyridine, see EXAMPLE 3. The (S)-epoxide (VIIIB) can be produced from the corresponding (S)-secondary alcohol (VIIIA) by reaction with potassium t-butoxide in THF at –20°, see EXAMPLE 11. Further the (S)-secondary alcohol (VIIIA) can be transformed to the corresponding (S)-ester (VIIIC) by reaction with the acylating reagents discussed above. For the (S)-ester (VIIIC), it is preferred that $R_N$ is —CO—$CH_3$.

CHART D discloses the process of reacting a carbamate of the formula $R_{oxa}$—NH—CO—O—$CH_2$—$X_1$ (IX) with either the (S)-secondary alcohol (VIIIA), the (S)-epoxide (VIIIB) or (S)-ester (VIIIC) to produce the corresponding (S)—oxazolidinone—$CH_2$—CO—$R_1$ (X). The carbamates (IX) are known to those skilled in the art or can be readily prepared from known compounds by methods known to those skilled in the art. It is preferred that $X_1$ is —H. $R_{oxa}$ is phenyl substituted with one —F and one substituted amino group. Substituted amino groups include 4-(benzyloxycarbonyl)-1-piperazinyl, 4-morpholinyl and 4-hydroxyacetylpiperazinyl. It is preferred that $R_{oxa}$ is 3-fluoro-4-[4-(benzyloxycarbonyl)-1-piperazinyl]phenyl or 3-fluoro-4-(4-morpholinyl)phenyl. The carbamate (IX) and the three carbon unit (VIIIA, VIIIb or VIIIC) is reacted by contacting the reactants with a base. The nature of which is not critical so long as it is strong enough to deprotonate the carbamate (IX). Operable bases are those whose conjugate acid has a $pK_a$ of greater than about 8. Preferred bases include compounds selected from the group consisting of:

alkoxy compounds of one thru seven carbon atoms, carbonate, methyl, sec-butyl and t-butyl carbanions, tri(alkyl)amines where the alkyl group is from 1 thru 4 carbon atoms, conjugate base of the carbamate (II),

DBU,

DBN,

N-methyl-piperidine,

N-methyl morpholine, 2,2,2-trichloroethoxide and $Cl_3C$—$CH_2$—$O^-$;

most preferred bases are where the base is alkoxy of four or five carbon atoms. It is preferred that the four and five carbon alcohol bases be t-amylate or t-butoxide. Sodium or potassium bases in combination with a lithium salt (such as lithium chloride or lithium bromide) can be used forming the lithium cation and base in situ. The nature of the solvent is not critical. Operable solvents include cyclic ethers such as THF, amides such as DMF and DMAC, amines such as triethylamine, acetonitrile, and alcohols such as t-amyl alcohol and t-butyl alcohol. The choice of solvent depends on the solubility of the carbamate (IX) and the three carbon unit (VIIIA, VIIIb or VIIIC) as is known to those skilled in the art.

CHART E discloses the reaction of the carbamate (IX) with either the (S)-phthalimide alcohol (IVC) or the (S)-phthalimide epoxide (IVD) to produce the (S)-ring-phthalimide (XI) which is then converted to the corresponding (S)—oxazolidinone—$CH_2$—NH—CO—$R_N$ (X) product which has pharmaceutical utility.

CHART F discloses the reaction of the carbamate (IX) with either (S)-protected alcohol (IVA) or (S)-imine of glydidylamine (IVB) to produce the corresponding (S)-oxazolidinone protected compound (XII) which is then transformed to the (S)-oxazolidinone free amine (XIII) which is then acylated as discussed above to produce the (S)—oxazolidinone—$CH_2$—NH—CO—$R_N$ (X) product which has pharmaceutical utility. These processes are the same as those for CHARTS D and E or are well known to those skilled in the art.

CHART G discloses the reaction of the carbamate (IX) directly with the (S)-3-carbon amino alcohol (V) to give the (S)-oxazolidinone free amine (XIII) which is then acylated to give the (S)—oxazolidinone—$CH_2$—NH—CO—$R_N$ (X). These processes are preformed in the same manner as previously disclosed.

CHART H discloses the reaction of teh isocynate (XIV) with (S)-secondary alcohol (VIIIA) to give the (S)-intermediate (XV) which is then transformed to the (S)—oxazolidinone—$CH_2$—NH—CO—$R_N$ (X), see EXAMPLES 6, 8 and 9.

CHART I discloses a reaction analogous to that of CHART E. Whereas the process of CHART E used a carbamate (IX), the process of CHART I uses an isocynate (XIV).

The (S)—oxazolidinone—$CH_2$—CO—amines (X) are known to be useful as antibiotic pharmaceuticals.

DEFINITIONS AND CONVENTIONS

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C(=$Z_1$) H. Groups $R_i$ and $R_j$ would represent monovalent variable substituents if attached to the formula $CH_3$—$CH_2$—C($R_i$)($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N^\#$=C($CH_3$)—CH=CCl—CH=$C^\#$H with the convention that the atoms marked with an asterisk (#) are bonded to each other resulting in the formation of a ring. Likewise, the cyclic molecular fragment, 4-(ethyl)-1-piperazinyl can be represented by —$N^{\#-(CH}_2)_2$—N($C_2H_5$)—$CH_2$—$C^\#H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol "- - -" or ". . . ". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents α-$R_{i-j}$ and β-$R_{i-k}$. When a bivalent variable, $R_i$, is defined to consist of two monovalent variable substituents, the convention used to define the bivalent variable is of the form "α-$R_{i-j}$:β-$R_{i-k}$" or some variant thereof. In such a case both α-$R_{i-j}$ and β-$R_{i-k}$ are attached to the carbon atom to give —C(α-$R_{i-j}$)(β-$R_{i-k}$)—. For example, when the bivalent variable $R_6$, —C(=$R_6$)— is defined to consist of two monovalent variable substituents, the two monovalent variable substituents are α-$R_{6-1}$:β-$R_{6-2}$, . . . α-$R_{6-9}$:β-$R_{6-10}$, etc, giving —C(α-$R_{6-1}$)(β-$R_{6-2}$)—, . . . —C(α-$R_{6-9}$)(β-$R_{6-10}$)—, etc. Likewise, for the bivalent variable $R_{11}$, —C(=$R_{11}$)—, two monovalent variable substituents are α$R_{11-1}$:β-$R_{11-2}$. For a ring substituent for which separate α and β orientations do not exist (e.g. due to the presence of a carbon carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO— . . . " means a lactone in which the carbonyl is bonded to $C_2$. However, when designated ". . . $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures are in degrees Centigrade.

TLC refers to thin-layer chromatography.

HPLC refers to high pressure liquid chromatography.

THF refers to tetrahydrofuran.

* indicates that the carbon atom is an enantiomeric carbon in the (S) configuration.

# indicates that the atoms marked with a (#) are bonded to each other resulting in the formation of a ring.

RING is defined in CHART J as the oxazolidinone ring, a 2,5-disubstituted-oxazolidinone.

DMF refers to dimethylformamide.

DMAC refers to dimethylacetamide.

Chromatography (column and flash chromatography) refers to purification/separation of compounds expressed as (support, eluent). It is understood that the appropriate fractions are pooled and concentrated to give the desired compound(s).

IR refers to infrared spectroscopy.

CMR refers to C-13 magnetic resonance spectroscopy, chemical shifts are reported in ppm (δ) downfield from TMS.

NMR refers to nuclear (proton) magnetic resonance spectroscopy, chemical shifts are reported in ppm (δ) downfield from tetramethylsilane.

TMS refers to trimethylsilyl.

—φ refers to phenyl ($C_6H_5$).

$[\alpha]_D^{25}$ refers to the angle of rotation of plane polarized light (specific optical rotation) at 25° with the sodium D line (589A).

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1 3-Fluoro-4-morpholinylaniline 3,4-Difluoronitrobenzene (25.196 g, 158.38 mmol) is added to a mixture of morpholine (60.0 ml, 688 mmol, 4.34 eq) in THF (30 ml) at −14°. The mixture is permitted to warm to 10° then maintained at 10–13° for 1 hr. A mixture of citric acid monohydrate (75 g, 357 mmol, 2.25 eq) in water (365 ml) is added with concomitant exotherm to 28°. The phases are separated and the aqueous phase is washed with toluene (95 ml). The organic phase is washed with water (315 ml) and concentrated under reduced pressure. Toluene (46 ml) and methanol (60 ml) are added followed by palladium on Carbon (5%, 50% water wet, 3.1603 g, 0.7426 mmol, 0.00469 eq) and the mixture sealed in a Parr shaker. Hydrogen pressure (40 psi) is applied and maintained while agitating for 42 min. The catalyst is then removed by filtration under reduced pressure and washed with toluene (60 ml). Heptane (150 ml) is added to the filtrate and the resultant slurry concentrated under reduced pressure. Heptane (300 ml) is added and the precipitate collected by filtration under reduced pressure and washed with heptane and dried to give the title compound, HPLC (stationary phase is 4.6×250 mm zorbax RX C-8 column; mobile phase is acetonitrile (650 ml), triethylamine (1.85 ml) and acetic acid (1.30 ml) and water of sufficient amount to make 1,000 ml; flow rate=3.0 ml/min; UV detection at 254 nm) RT=1.08 min, >99.3 area); NMR (Pyridine-$D_5$) 2.95–2.98, 3.80–3.83, 5.38, 6.68, 6.78 and 6.90 δ; CMR (Pyridine-$D_5$) 52.43, 67.33, 103.31, 110.63, 121.29, 130.80, 146.23 and 157.72 δ.

Preparation

2 N-Carbomethoxy-3-fluoro-4-morpholinylaniline (IX)

3,4-Difluoronitrobenzene (PREPARATION 1, 24.967 g, 156.94 mmol) is added to a mixture of morpholine (60.0 ml, 688 mmol, 4.38 eq) in THF (30 ml) at −6°. The mixture is permitted to warm to 10° over 2 hrs then maintained at 10° for ½ hr. A mixture of citric acid monohydrate (75 g, 357 mmol, 2.27 eq) in water (365 ml) is added with concomitant exotherm to 28°. The phases are separated and the aqueous washed with toluene (95 ml). The organic phases are washed with water (315 ml), the aqueous back wash extracted with toluene (95 ml) and concentrated under reduced pressure. Toluene (76 ml) and methanol (60 ml) are added followed by palladium on carbon (5%, 50% water wet, 3.1370 g, 0.7371 mmol, 0.00470 eq) and the mixture sealed in a Parr shaker. Hydrogen pressure (40 PSI) is applied and maintained while agitating for 4.5 hrs. The catalyst is then removed by filtration under reduced pressure and washed with toluene (100 ml). The mixture is cooled to 2° and a mixture of aqueous potassium carbonate (47%, 17.1 ml, 85 mmol, 0.54 eq) and water (150 ml) is added. Methyl chloroformate (16.4 ml, 212 mmol, 1.35 eq) is then added while maintaining the temperature at about 3–3.5°. The resultant slurry is permitted to warm to 20–25° and stirred 17 hrs. The mixture is warmed to 75° to give a solution, then cooled to 46°, heptane (333 ml) added, then the mixture cooled to 0°, the precipitate collected by filtration with reduced pressure, washed with heptane (100 ml cooled to 5°) then water (230 ml cooled to 5°) and dried to give the title compound, TLC (silica gel; methanol/methylene chloride, 5/95) $R_f$=0.74 (one spot); NMR ($CDCl_3$) 3.03, 3.76, 3.86, 6.75, 6.87, 6.98, 7.27; CMR ($CDCl_3$) 51.18, 52.42, 67.03, 107.81, 114.56, 119.00, 133.25, 135.77, 154.07, 155.70, Preparation 3 3-Fluoro-4-morpholinylphenylisocyanate (XIV)

A mixture of 3-Fluoro-4-morpholinylaniline (PREPARATION 1, 12.01 g, 61.21 mmol) in methylene chloride (100 ml) is added to a mixture of phosgene (1.93 M in toluene, 63.4 ml, 122.4 mmol, 2.00 eq) in p-chlorotoluene (60 ml) over 15 min, a while maintaining the temperature from about −12 to 3°. The material is rinsed in with methylene chloride (30 ml). The mixture is then warmed to 130° under atmospheric pressure with concomitant distillation of methylene chloride, phosgene, toluene and hydrogen chloride gas into a caustic scrubber. The mixture is cooled to 25° and filtered. The precipitate is washed with methylene chloride (3×15 ml). The filtrate is concentrated under reduced pressure. Heptane (200 ml) is added to the concentrated filtrate and the resultant slurry cooled to −32°. The product is collected by filtration with reduced pressure, washed with heptane cooled to −30°, and dried in a nitrogen stream to give the title compound, HPLC (stationary phase is 4.6×250 mm zorbax RX C-8 column; mobile phase is acetonitrile (650 ml), triethylamine (1.85 ml) and acetic acid (1.30 ml) and water of sufficient amount to make 1,000 ml; flow rate=3.0 ml/min; UV detection at 254 nm) RT=1.08 min. Upon derivatizing as N-carbomethoxy-3-fluoro-4-morpholinylaniline by dissolving in methanol; NMR ($CDCl_3$) 3.05, 3.86 and 6.78–6.89 δ; CMR ($CDCl_3$) 50.90, 66.89, 113.11, 119.15, 120.83, 124.67, 127.65, 138.06 and 155.40 δ; MS (EI), m/z (relative intensity) 222 (37) and 164 (100).

Example 1

(S)-1-Amino-3-chloro-2-propanol hydrochloride (V)

(S)-Epichlorohydrin (III, 44.978 g, 486.1 mmol, 98.9% enantiomeric excess, 99.3 chemical % purity) is added to a mixture of benzaldehyde (I, 50.0 ml, 492 mmol, 1.012 eq), ethanol (163 ml) and aqueous ammonia (II, 29.8 wt%, 50 ml, 787.4 mmol, 1.62 eq) at 18° over 10 min with an exotherm to 22°. The reaction mixture is permitted to exotherm to 34° over 1.5 hrs, warmed to 42°, stirred at 20–25° for 20.5 hrs, then warmed to 74° and immediately allowed to cool. The mixture is concentrated under reduced pressure to give (S)-1-bezalimino-3-chloro-2-propanol (IVA). Water (382 ml) and hydrochloric acid (37.7 wt %, 76.2 ml, 938 mmol, 1.93 eq) is added to the concentrate and the mixture stirred at 20–25° for 2 hrs. Toluene (150 ml) is added and the phases are separated. The organic phase is washed with water (15 ml) and the combined aqueous washed with toluene (2×150 ml), back extracting each organic extract with water (15 ml). The combined aqueous extracts are concentrated under reduced pressure. Ethanol (200 ml) is added to the concentrate and the mixture concentrated under reduced pressure. Ethanol (300 ml) is added to the concentrate and the mixture warmed to reflux. The mixture is cooled to −30° and the precipitate collected by filtration with reduced pressure, washed with −30° ethanol (2×60 ml) and dried in a nitrogen stream to give a white solid, mp=132–141°; NMR ($CD_3OD$) 2.96, 3.21, 3.57–3.64 and 4.03–4.09 δ; CMR ($CD_3OD$) 43.52, 46.91 and 68.72 δ; MS (CI, $NH_3$), M/Z (relative intensity) 129 (24), 127 (69), 112 (61), 110 (100); $[\alpha]^{25}_D$=−22 (c=1.00, $H_2O$).

Example 2

(S)-1-Acetamido-2-hydroxy-3-chloropropane (VIIIA)

Triethylamine (10.5 ml, 75.3 mmol, 1.11 eq) is added to a slurry of (S)-1-amino-3-chloro-2-propanol hydrochloride (V, EXAMPLE 1, 9,938 g, 68.059 mmol) in THF (80 ml) at −40° and the mixture stirred for 5 min at −40°. Acetic anhydride (6.78 ml, 71.86 mmol, 1.056 eq) is then added at −40° and the mixture allowed to warm to 20–25° over 1.5 hrs. The precipitate is removed by filtration with reduced pressure and washed with THF. The filtrate is treated with magnesol (5.69 g), which is removed by filtration with reduced pressure and washed with THF (2×60 ml). The filtrate is then concentrated under reduced pressure. The concentrate is purified by flash chromatography (silica gel; eluting with a gradient of 75–100% ethyl acetate/cyclohexane) to give the title compound, NMR ($CDCl_3$) 2.03, 3.32, 3.50–3.57, 3.55, 3.91–4.13, 5.01 and 7.09 δ; CMR ($CDCl_3$) 23.00, 43.31, 46.52, 70.65 and 172.40 δ; MS (CI, $NH_3$), M/Z (relative intensity), 171 (41.6), 169 (100), 154 (22.4), 152 (48.1); $[\alpha]^{25}_D$=−7.44 (c=1.00, $H_2O$).

Example 3

(±)-1-Acetamido-2-acetoxy-3-chloropropane (VIIIC)

Acetic anhydride (13 ml) is added to a thin slurry of (±)-1-amino-3-chloro-2-propanol hydrochloride ((±)-V, EXAMPLE 5, 5.0110 g, 34.317 mmol) in pyridine (20 ml) while maintaining the temperature in the range of 20–50°. The mixture is stirred at 20–25° for 18 hours, then water (14 ml) is added with an exotherm to 65°. The mixture is concentrated under reduced pressure and water (50 ml) is added. The pH is adjusted to 0.89 with hydrochloric acid (37.7%, 1.467 g, 15.17 mmol, 0.442 eq) at 0°. The mixture is extracted with methylene chloride (4×50 ml), the extracts dried over sodium sulfate and concentrated under reduced pressure. Ethyl acetate (20 ml) and heptane (20 ml) are added, the mixture seeded, then heptane (40 ml) is added to the resultant slurry. The precipitate is collected by filtration with reduced pressure, washed with heptane and dried to give a the title compound, mp=68.0–69.5°; TLC (silica gel; ethyl acetate, iodine char) $R_f$=0.39 (one spot); NMR 2.00, 2.21, 3.52, 3.62, 3.70, 5.10 and 6.33 δ; CMR 20.93, 23.10, 40.47, 43.53, 71.95, 170.45 and 170.71 δ; MS (CI, $NH_3$) m/z (relative intensity) 213 (36), 211 (100), 196 (18) and 194 (53).

Example 4

(S)-1-Phthalimido-3-chloro-2-propanol (S)-(IVC)

S-epichlorohydrin (III, 98.9% enantiomerically pure, 99.3 chemical % purity, 4.9605 g, 53.61 mmol) is added to a slurry of potassium phthalimide (VI, 5.031 g, 27.161 mmol, 0.507 eq) and phthalimide (VI, 11.836 g, 80.45 mmol, 1.5006 eq) in DMF (32 ml) and the mixture stirred at 50° for 4.5 hrs. The mixture is added to methylene chloride (50 ml) and water (50 ml) added. The solids are removed by filtration with reduced pressure and washed with methylene chloride (20 ml). The phases are separated in the filtrate and the aqueous washed with methylene chloride (50 ml). The combined organics were washed with water (50 ml) and the aqueous backextraceted with methylene chloride (50 ml) after adding water (25 ml). The combined organics are dried over sodium sulfate and saturated with hydrogen chloride gas at 6°. Water (100 ml) is added and the phases separated. The aqueous phase is washed with methylene chloride (2×50 ml) and the combined organic phases are dried over sodium sulfate. The organic phase is concentrated under reduced pressure and toluene added (77 ml). The mixture is concentrated under reduced pressure to 31 g net weight and toluene (50 ml) and heptane (75 ml) added. The solids are filtered off and washed with toluene/heptane (1/1, 20 ml). The filtrate is concentrated under reduced pressure to 17 g net weight, heptane (100 ml) added and the mixture concentrated under reduced pressure to 15 g net weight. Heptane (100 ml) and methylene chloride (100 ml) is added and the mixture concentrated under reduced pressure to 130 g net weight. The solids are filtered off and washed with heptane/methylene chloride (2/1, 3×15 ml). The filtrate is concentrated under reduced pressure to 11 g net weight and toluene (90 ml) then heptane (400 ml) added. The resultant slurry is then cooled to –20° and the product collected by filtration under reduced pressure, washed with heptane and dried to give a crude solid. Flash chromatography of the crude solid (silica gel; eluting with a gradient of 15–45% ethyl acetate/cyclohexane) gives the title compound as an analytical sample, NMR 3.11, 3.62, 3.68, 3.87, 3.95, 4.14–4.20, 7.70–7.76 and 7.82–7.88 δ; CMR 41.61, 47.27, 69.68, 123.53, 131.83, 134.26 and 168.65 δ; MS (CI, $NH_3$), M/Z (relative intensity) 259 (1.4), 257 (17), 242 (0.11), 240 (0.31), 221 (100); $[\alpha]^{25}_D$=–33 (C=0.712, $CHCl_3$). NMR of the mosher ester derivative showed the product to have an enantiomeric purity of 96.2% upon comparison to the NMR of the mosher ester of the racemate.

Example 5

(±)-1-Amino-3-chloro-2-propanol hydrochloride
(±)-(V)

A slurry of (±)-1-phthalimido-3-chloro-2-propanol (IVC, 40.018 g, 166.98 mmol) in hydrochloric acid (37.5 wt %, 79 ml, 968 mmol, 5.80 eq) and water (82 ml) is stirred at 109° for 5 hrs. The mixture is cooled to 22° and the precipitate is removed by filtration with reduced pressure and washed with water (40 ml). The filtrate is concentrated under reduced pressure to 26 g net weight and ethanol (100 ml) added. The mixture is warmed to 75° to give a solution then cooled to –12° and the resultant precipitate collected by filtration with reduced pressure, washed with ethanol cooled to –12° and dried to give the title compound, mp=101–104°; NMR ($CD_3OD$) 2.96, 3.21, 3.57–3.64 and 4.03–4.09 δ; CMR ($CD_3OD$) 43.54, 46.95 and 68.71 δ; MS (CI, $NH_3$), M/Z (relative intensity) 129 (12), 127 (39), 112 (56), 110 (100).

Example 6

(S)-N-Carbo(1'-acetamido-3'-chloro-2'-propoxy)-3-fluoro-4-morpholinylaniline ((S)-XV)

Acetyl chloride (0.3297 g, 4.20 mmol, 1.019 eq) is added to a slurry of (S)-1-Amino-3-chloro-2-propanol hydrochloride (V, EXAMPLE 1, 0.6020 g, 4.12 mmol) and triethylamine (1.26 ml, 9.04 mmol, 2.19 eq) in acetonitrile (70 ml) at –40 °.

The mixture is then warmed to 3–6°, stirred several hours, warmed to 22° and 3-fluoro-4-morpholinylphenylisocyanate (XIV, PREPARATION 3, 1.0152 g, 4.568 mmol, 1.108 eq) added. The mixture is warmed to 64°, stirred 10 min, then concentrated under reduced pressure to about 25 ml. 3-Fluoro-4-morpholinylphenylisocyanate (XIV, 0.0907 g, 0.408 mmol, 0.09887 eq) is then added and the mixture stirred at 65° for 17 hrs. Pentanol (1.34 ml, 12.33 mmol, 2.99 eq) is added and the mixture stirred at 65° for 1.7 hrs. Water (5 ml) is added and the mixture cooled to –4°. Water (38 ml) and heptane (30 ml) were added and the mixture warmed to 15° and stirred 1 hr. The resulting precipitate is collected by filtration under reduced pressureand washed with heptane and water and dried to give a solid. The filtrate is concentrated under reduced pressure to 50 ml total volume and the precipitate collected by filtration under reduced pressure, washed with water (10 ml) and heptane (10 ml) and dried to give a brown solid. A portion of the first solids (0.9404 g) and the second solids (0.4018 g) is dissolved in acetonitrile (15 ml) at 76°, then cooled to –10° and the precipitate collected by filtration under reduced pressure, washed with acetonitrile cooled to –10° and dried to give the title compound, HPLC (stationary phase is 4.6×250 mm zorbax RX C-8 column; mobile phase is acetonitrile (650 ml), triethylamine (1.85 ml) and acetic acid (1.30 ml) and water of sufficient amount to make 1,000 ml; flow rate=3.0 ml/min; UV detection at 254 nm)=92.3 area %).

Example 7

(S)-N-Carbo(1'-acetamido-3'-chloro-2'-propoxy)-3-fluoro-4-morpholinylaniline ((S)-XV)

A mixture of (S)-1-acetamido-3-chloro-2-propanol (VIIIA, EXAMPLE 2, 1.024 g, 6.754 mmol, 1.00 eq) and 3-fluoro-4-morpholinylphenylisocynate (XIV, PREPARATION 3, 1.6756 g, 7.539 mmol, 1.12 eq) in acetonitrile (25 ml) is stirred at 60° for 46 hrs. The resultant slurry is cooled to −31°, the precipitate collected by filtration with reduced pressure, washed with acetonitrile cooled to −13° C. (20 ml) and dried to give the title compound, NMR (DMSO-D6) 1.83, 2.93, 3.2–3.5, 3.73, 3.78, 3.88, 4.99, 6.97, 7.20, 7.36, 8.07 and 9.80 δ; CMR (DMSO-D6) 22.42, 39.6, 44.71, 50.77, 66.15, 71.81, 106.49, 114.23, 119.21, 134.18, 134.59, 152.57, 154.65 and 169.67 δ; MS (CI, $NH_3$), M/Z (relative intensity) 376 (27.0), 374 (85.9), 339 (12.2), 338 (80.8) and 223 (17.2); $[\alpha]^{25}_D$=−4.08 (C=0.930, DMF).

Example 8

(S)-N-[[3-Fluoro-4-(4-morpholinyl)phenyl]-2-oxo-5-oxazolidinyl]methyl]acetamide ((S)-X)

A solution of sodium t-butoxide (0.0854 g, 0.889 mmol, 1.05 eq) in ethanol (0.60 ml) is added to a slurry of (S)-N-carbo(1'-acetamido-3'-chloro-2'-propoxy)-3-fluoro-4-morpholinylaniline ((S)-XV), EXAMPLE 7, 0.3176 g, 0.850 mmol) in ethanol (4.6 ml) at 65° and is rinced in with ethanol (0.50 ml). The mixture is stirred 28 min and cooled to 0°. Citric acid monohydrate (0.1943 g, 0.925 mmol, 1.09 eq) is added and the resulting slurry concentrated under reduced pressure to 1.30 g net weight. Water (10 ml) and methylene chloride (10 ml) is added, the phases separated and the aqueous phase washed with methylene chloride (2×10 ml). The combined organic phases are dried over sodium sulfate and concentrated under reduced pressure to a solid. The solid is dissolved in ethyl acetate (8.4 ml) at 70°, solution cooled to 50°, seeded, further cooled to −28°, the precipitate collected by filtration with reduced pressure, washed with ethyl acetate previously cooled to −30° and dried to give the title compound, HPLC (100.7 wt %, 99.9 area %; NMR ($CDCl_3$) 2.04, 3.04, 3.65, 3.77, 3.86, 4.02, 4.74–4.82, 6.80, 6.91, 7.06 and 7.42 δ; CMR ($CDCl_3$) 22.99, 41.88, 47.64, 50.96, 66.94, 72.08, 107.55, 113.98, 118.83, 132.93, 136.55, 154.55, 155.44 and 171.40 δ; MS (EI), M/Z (relative intensity) 337 (16.9), 293 (74.4), 234 (37.5), 209 (100); $[\alpha]^{25}_D$=−15.8 (C=0.903, ethanol).

Example 9

(S)-N-[[3-Fluoro-4-(4-morpholinyl)phenyl]-2-oxo-5-oxazolidinyl]methyl]acetamide (IV)

Following the general procedure of EXAMPLE 8 and making non-critical variations the title compound is obtained, NMR 2.02, 3.04, 3.65, 3.77, 3.86, 4.02, 4.74–4.82, 6.74, 6.91, 7.06 and 7.42 δ); CMR 23.02, 41.89, 47.65, 50.97, 66.87, 72.06, 107.48, 114.01, 118.76, 132.85, 136.48, 154.52, 155.38 and 171.34 δ; MS (CI, $NH_3$), M/Z (relative intensity) 338 (100), 294 (86.8); $[\alpha]^{25}_D$=−15.2 (C=0.783, ethanol).

Example 10

(±)-N-(2-Hydroxy-3-chloro)acetamide (VIIIA)

To a slurry of (±)-1-Amino-3-chloro-2-propanol hydrochloride (V, EXAMPLE 5, 47.71 g, 326.74 mmol) in THF (381 ml) at −40° is added triethylamine (36.496 g, 360.67 mmol, 1.104 eq) followed by acetic anhydride (35.007 g, 342.90 mmol, 1.049 eq) while maintaining the temperature at <−30°. The mixture is stirred 15 min at −30°, then allowed to warm to 20° over 1 hr. The mixture is stirred at 20–25° for 3 hours, then the precipitate is removed by vacuum filtration through a medium frit and washed with THF (175 ml). The filtrate is concentrated under reduced pressure to and toluene (195 ml) added. The mixture is concentrated under reduced pressure to and toluene (250 ml) is added. The mixture is concentrated under reduced pressure and toluene (250 ml), methanol (40 ml) and ethyl acetate (10 ml) added. The mixture is cooled to −20°, seeded, heptane (200 ml) added at −30°, the mixture cooled to −33° and the precipitate collected by vacuum filtration, washed with heptane (100 ml) and dried. This solid (44.818 g) is dissolved in toluene (250 ml) and methanol (120 ml) and concentrated under reduced pressure. The mixture is cooled to −30°, seeded and heptane (180 ml) is added the precipitate collected by vacuum filtration at −30°, washed with heptane (100 ml) and dried to give a solid, mp=50.1–52.3°; TLC (silica gel; methanol/methylene chloride (5/95), iodine char) $R_f$=0.23 (single more polar spot identified as 1.1 wt% triethylammonium acetate by NMR); NMR ($CDCl_3$) 2.03, 3.33, 3.54, 3.95, 4.73 and 6.93 δ; CMR ($CDCl_3$) 23.01, 43.32, 46.48, 70.72 and 172.37 δ; MS (CI, $NH_3$) m/z (relative intensity) 154 (34), 152 (100).

Example 11

(±)-Glycicylacetamide (VIIIB)

To a solution of (±) 1-acetamido-3-chloro-2-propanol (V, EXAMPLE 10, 10.344 g, 68.24 mmol) in tetrahydrofuran (21 ml) at −40° Is added a solution of potassium t-butoxide in THF (1.0 M, 65 ml, 65 mmol, 0.95 eq). The mixture was warmed to −20° and stirred for 15 min then cooled to −37° and silica gel (18.5 g) is added. The solids are removed by vacuum filtration and washed with ethyl acetate (1,000 ml). The filtrate is concentrated and the precipitate removed by vacuum filtration. The filtrate is concentrated and heptane (50 ml) is added. The mixture is seeded, sonicated, and the precipitate collected by vacuum filtration, washed with heptane and dried in a nitrogen stream to give the title compound, mp=34.6–37.3°; TLC (silica gel; methanol/methylene chloride (5/95), iodine char) $R_f$=0.24; NMR 2.01, 2.59, 2.80, 3.10–3.13, 3.24–3.29, 3.7–3.9, 6.19 δ; CMR 23.07, 40.67, 45.19, 50.61 and 170.54 δ.

Example 12

(±)-N-[[3-(3-Fluoro-4-morpholinylphenyl)-2-oxo-5-oxazolidinyl]methyl]acetamide (X)

To a solution of (±)-glycidylacetamide (VIIIB, EXAMPLE 11, 0.1571 g, 1.365 mmol) in THF (1.63 ml) at −78° is added N-carbomethoxy-3-fluoro-4-morpholinylaniline (IX, PREPARATION 2, 0.4358 g, 1.71 mmol, 1.26 eq) and lithium t-butoxide (0.1267 g, 1.583 mmol, 1.16 eq). The reaction mixture is then stirred at 0 to 11° for 17.5 hrs at which point HPLC showes an 80% yield of (±)-N-[[3-(3-fluoro-4-morpholinylphenyl)-2-oxo-5-oxazolidinyl]methyl]acetamide (retention time=0.97 min; method B; Stationary phase: 4.6×250 mm Zorbax RX C-8 column; mobile phase: 650 ml acetonitrile, 1.85 ml triethylamine, 1.30 ml acetic acid, water sufficient to make 1000 ml; flow rate: 3.0 ml/min; UV detection at 254 nm). The title compound is isolated by means known to those skilled in the art.

Example 13

(S)-N-[[3-(3-Fluoro-4-morpholinylphenyl)-2-oxo-5-oxazolidinyl]methyl]acetamide (X)

Step A: (S)-N-(2-Hydroxy-3-chloro)acetamide (VIIIA)

Following the general procedure of EXAMPLE 10 and making non-critical variations but starting with (S)-1- amino-3-chloro-2-propanol hydrochloride (V, EXAMPLE 1), the title compound is obtained.

Step B: (S)-Glycidylacetamide (VIIIB)

Following the general procedure of EXAMPLE 11 and making non-critical variations but starting with (S)-N-(2-Hydroxy-3-chloro)acetamide (VIIIA, Step A), the title compound is obtained.

Step C: (S)-N-[[3-(3-Fluoro-4-morpholinylphenyl)-2-oxo-5-oxazolidinyl]methyl]acetamide (X)

Following the general procedure of EXAMPLE 12 and making non-critical variations but starting with (S)-Glycidylacetamide (VIIIB, Step B), the title compound is obtained.

Example 14

(S)-1-Acetamido-2-acetoxy-3-chloropropane (VIIIC)

Following the general procedure of EXAMPLE 3 and making non-critical variations but starting with (S)-1-Amino-3-chloro-2-propanol hydrochloride (V, EXAMPLE 1), the title compound is obtained.

Example 15

(S)-1-Amino-3-chloro-2-propanol hydrochloride (S)-(V)

Following the general procedure of EXAMPLE 5 and making non-critical variations but using (S)-1-phthalimido-3-chloro-2-propanol (S)-(IVC, EXAMPLE 4) the title compound is obtained.

CHART A

O=CH—X$_0$
(I)

+

NH$_3$
(II)

+

X$_2$—CH$_2$—C$^{*\#}$H—CH$_2$—O$^{\#}$—
(III)

↓

X$_2$—CH$_2$—C$^*$H(OH)—CH$_2$—N=CH—X$_0$
(IVA)

↓

-continued

X$_2$—CH$_2$—C$^*$H(OH)—CH$_2$—NH$_3^+$
(V)

—O$^{\#}$—CH$_2$—C$^{*\#}$H—CH$_2$—N=CH—X$_0$
(IVB)

CHART B phthalimide
(VI)

+

X$_2$—CH$_2$—C$^{*\#}$H—CH$_2$—O$^{\#}$—
(III)

↓

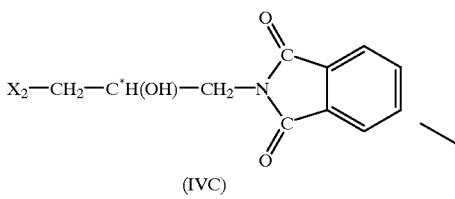
(IVC)

↓

X$_2$—CH$_2$—C$^*$H(OH)—CH$_2$—NH$_3^+$
(V)

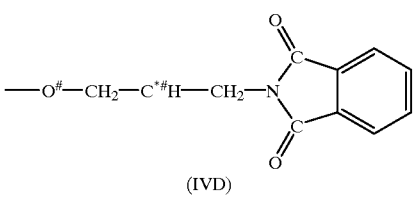
(IVD)

CHART C

X$_2$—CH$_2$—C$^*$H(OH)—CH$_2$—NH$_3^+$
(V)

↓

X$_2$—CH$_2$—C$^*$H(OH)—CH$_2$—NH—CO—R$_N$
(VIIIA)

↓

—O$^{\#}$—CH$_2$—C$^*$H—CH$_2$—NH—CO—R$_N$
(VIIIB)

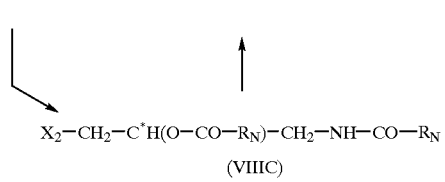
(VIIIC)
CHART D
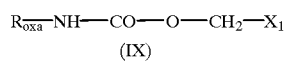
(IX)
+
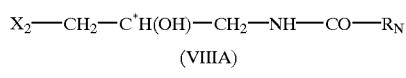
(VIIIA)
or
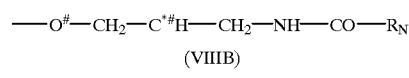
(VIIIB)
or
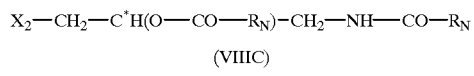
(VIIIC)
↓
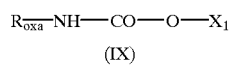
(X)
CHART E
R<sub>oxa</sub>—NH—CO—O—X<sub>1</sub>
(IX)
+
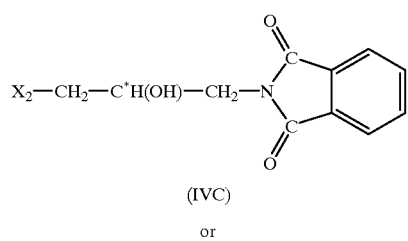
(IVC)
or
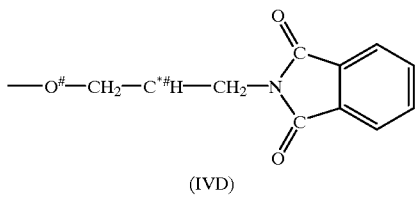
(IVD)
↓
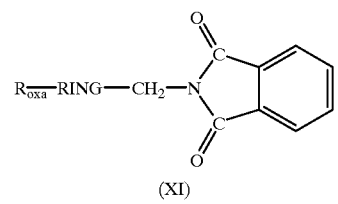
(XI)
↓
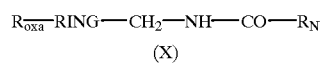
(X)
CHART F
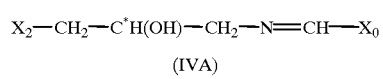
(IVA)
or
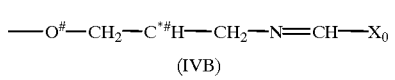
(IVB)
+
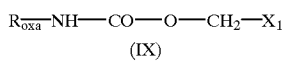
(IX)
↓
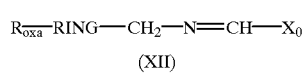
(XII)
↓

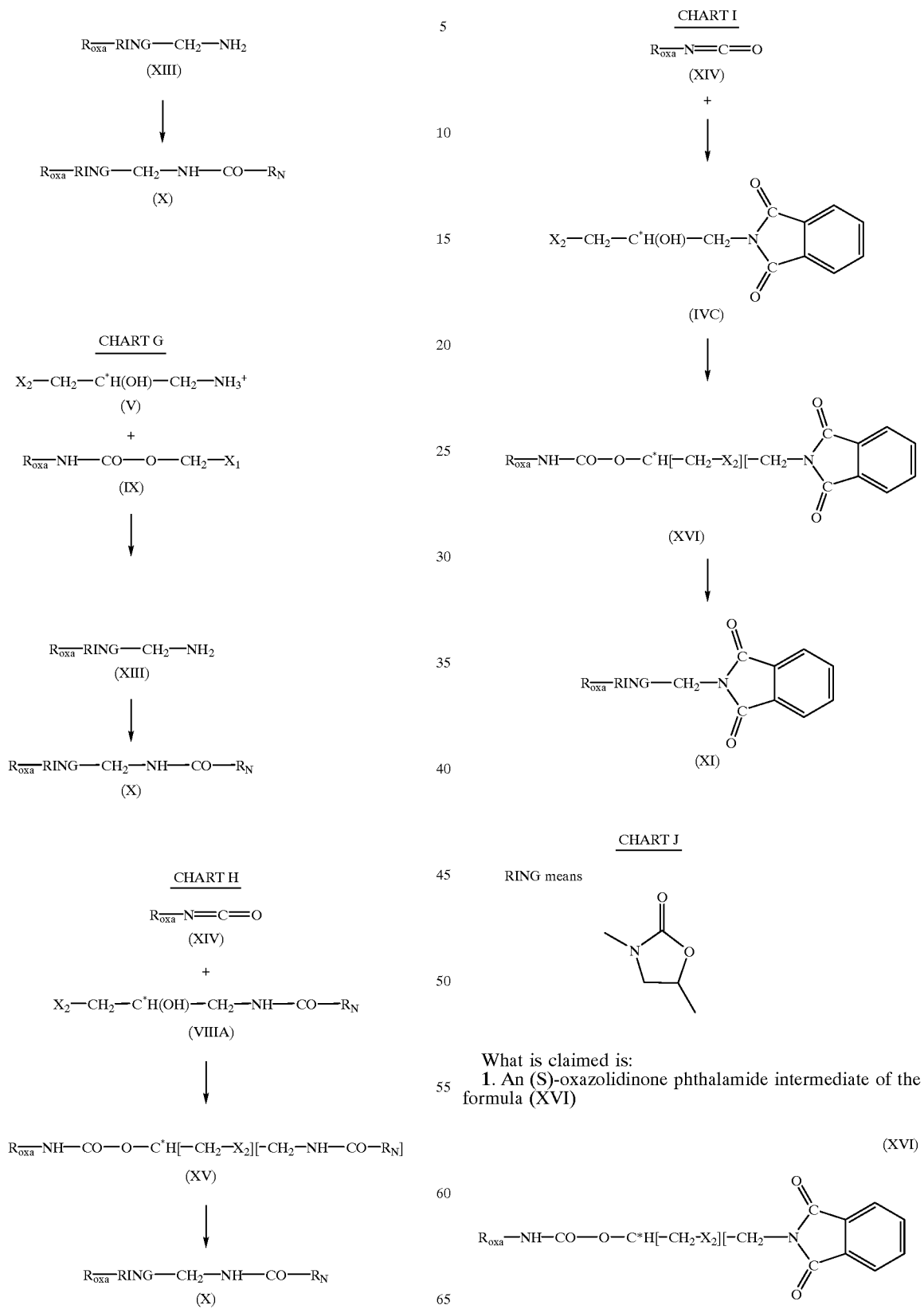
What is claimed is:
1. An (S)-oxazolidinone phthalamide intermediate of the formula (XVI)

where:
- (I) $R_{oxa}$ is phenyl substituted with one —F and one substituted amino group;
- (II) $X_2$ is:
  - (A) —Cl,
  - (B) —Br,
  - (C) p—$CH_3$—$\phi$—$SO_2$—,
  - (D) m—$NO_2$—$\phi$—$SO_2$—.

2. An oxazolidinone phthalamide intermediate (XVI) according to claim 1 where $R_{oxa}$ is:
- 3-fluoro-4-[4-(benzyloxycarbonyl)-1-piperazinyl]phenyl,
- 3-fluoro-4-(4-morpholinyl)phenyl and
- 3-fluoro-4-(4-hydroxyacetylpiperazinyl)lphenyl.

3. An oxazolidinone phthalamide intermediate (XVI) according to claim 1 where $X_2$ is —Cl.

* * * * *